United States Patent [19]

Cheng

[11] Patent Number: 4,666,844

[45] Date of Patent: May 19, 1987

[54] PROCESS FOR REGENERATING CEREALS

[75] Inventor: David S. K. Cheng, Foster City, Calif.

[73] Assignee: Sungene Technologies Corporation, Palo Alto, Calif.

[21] Appl. No.: 648,388

[22] Filed: Sep. 7, 1984

[51] Int. Cl.$^4$ .......................... C12N 5/00; C12N 5/02
[52] U.S. Cl. .................................. 435/240; 435/241; 800/1
[58] Field of Search .................... 435/240, 241; 800/1

[56] References Cited

PUBLICATIONS

Maddock et al., 1983, *J. Exp. Bot.*, v 34, 915–26, (Ref. #20).
Evans et al., 1981, "Growth and Behavior of Cell Cultures: Embryogenesis and Organogenesis" in *Plant Tissue Culture*, Thorpe, ed. Academic Press, pp. 45–113.
Conger (ed.), 1981, *Cloning Agricultural Plants via in vitro Techniques*, p. 55.
The Yearbook of Agriculture 1961 Congressional Document, No. 29, 2 plates.

Primary Examiner—Thomas G. Wiseman
Assistant Examiner—David T. Fox
Attorney, Agent, or Firm—Robbins & Laramie

[57] ABSTRACT

The present invention relates to the regeneration of cereals including barley, corn, wheat, rice and sorghum. The process comprises the steps of:

(a) culturing tissue obtained from a cereal plant on an induction medium comprising mineral salts, vitamins, sucrose and a hormone in an amount sufficient to ensure callus formation, (b) culturing the callus on a series of media, said series comprising at least one medium and each medium comprises mineral salts, vitamins, sucrose and a hormone in an amount sufficient to insure differentiating to plantlets having shoots and roots at the completion of the series, and (c) culturing the plantlets on an establishment medium comprising mineral salts, vitamins and sucrose, whereby the plantlets are established so that they can be transplanted to soil.

40 Claims, 1 Drawing Figure

PROCESS FOR REGENERATING CEREALS

BACKGROUND OF THE INVENTION

1. Field of the Invention

The present invention relates to a general process for regenerating cereals, e.g., barley, corn, wheat, rice, sorghum, etc., and to plants produced by the process. More particularly, the invention relates to the use of tissue and cell culture for the regeneration of cereal plantlets from many varieties of cereals.

2. Description of the Prior Art

Plant regeneration from cells in culture is essential for the application of somatic hybridization, for the production of new varieties through somoclonal variation, and for the use of genetic engineering in producing new varieties.

In recent years, plant cell culture successes have had a considerable influence on the respective roles of cell and organism in control of plant growth and development. This concept was supported when isolated plant cells were shown to be amenable to in vitro cultivation and complete plants could be regenerated from cultures derived from somatic cells, either directly via somatic embryogenesis or indirectly via organogenesis. Generally, the regeneration pathway of choice is determined empirically by the manipulation of extrinsic factors, espectially growth regulators. Early investigations of certain plant species have suggested that exogenous auxin concentration is the major factor controlling somatic embryogenesis, such that its reduction leads to the initiation of embryoid formation. In other species, exposure to a definite balance of auxin and cytokinin leads to the formation of organogenesis (shoots, then roots). Many systems that have been developed are at best genus-specific. A few systems with some variations have been found to be applicable to some species of a few genera. However, no prior art system has been found to be generally applicable to most cereals.

One approach which has been tried for several different cereals is the induction of callus on a medium containing a hormone and the regeneration of plants on a medium lacking a hormone. This has been shown by Wernicke et al., *Nature* 287, 138 (1980) for sorghum using an MS medium and 2,4-dichlorophenoxyacetic acid (2,4-D) as the hormone and leaf tissue as the explant source. This technique has also been used for rice by Nishi et al., *Bot. Mag. Tokyo* 86, 183 (1973) and Heyser et al., *Plant Sci. Letts.*, 29, 175 (1983). Nishi et al. utilized seed as the explant source, and LS medium containing myo-inositol and thiamine and either 2,4-D, alpha-naphthalene acetic acid (NAA), or indoleacetic acid (IAA) as the hormone. Nabors et al., *Planta.*, 157, 385 (1983) have also used this approach for wheat, rice, oats and millet. Nabors et al. utilized seedling roots as the source of explant tissue, LS medium and 2,4-D or 2,4,5-trichlorophenoxyacetic acid (2,4,5-T) in combination with kinetin or IAA or tryptophan as the hormone.

Ishii, *Proc. 5th Int. Cong. Plant Tissue & Cell Culture* p. 185 (1982) utilized wheat, barley or oat seedlings as the source of explant tissue, MS medium and 2,4-D as the hormone. Similarly, Ozias-Akins et al, *Protoplasma* 115, 104 (1983) used immature embryo of wheat as the explant tissue, MS or B5 medium and 2,4-D as the hormone. Dale et al., *Z. Pflanzenphysiol.* 94, 65 (1979) utilized immature embryo of wheat as the explant tissue, B5 medium and 2,4-D as the hormone.

A similar approach which has been utilized to regenerate corn and barley is to use a lower amount of hormone in the regeneration medium than was used in the callus induction medium. This technique has been described by Green et al., *Crop Sci.* 15, 417 (1975) for corn immature embryos, MS medium and 2,4-D as the hormone. This technique has been described in an abstract of Ching-san et al. for barley immature endosperm, MS medium and an auxin.

A third approach is to induce callus formation and plant regeneration on medium containing different hormones. Masteller et al., *Plant Physiol* 45, 362 (1970) utilized sorghum shoot tissue as the explant tissue, revised MS medium, a mixture of 2,4-D and coconut milk for callus induction, and a mixture of NAA and coconut milk for plant regeneration. Ram et al., *Z. Pflanzenphysiol.* 113, 315 (1984) utilized rice seed as the explant tissue, LS medium, a mixture of 2,4-D and kinetin as the hormone for callus induction, and a mixture of IAA and 6-benzyl adenine (BA) as the hormone for plant regeneration. Yan et al., *Plant Sci. Letts.* 25, 187 (1982) utilized rice leaf blade as the explant tissue, modified MS medium, a mixture of 2,4-D, NAA and IAA as the hormone for callus induction and a mixture of IAA, BA and giberellic acid ($GA_3$) as the hormone for plant regeneration. McHugen et al., *Ann. Bot.* 51, 851 (1983) describe the use of wheat node tissue, MS medium, 2,4-D as the hormone for callus induction, and a mixture of IAA and kinetin as the hormone for plant regeneration.

A fourth approach involves the use of at least three medium in sequence for plant regeneration. The media may be used for callus induction, callus maintenance, shoot formation and root formation. An example in rice has been shown by Bajaj et al., *Theor. Appl. Genet.* 58, 17 (1980). Bajaj et al. utilized rice embryo and MS medium containing yeast extract. 2 mg/l 2,4-D was utilized for callus induction, 1 mg/l 2,4-D for callus maintenance, and IAA and kinetin for plant regeneration. Ahloowalia, *Crop Sci.* 22, 405 (1982) utilized wheat immature embryos as explant tissue, one-half MS medium, a mixture of 2,4-D, IAA and kinetin for callus induction, a mixture of 2,4-D and zeatin for shoot formation, and NAA for root formation. Sears et al., *Crop Sci.* 22, 546 (1982) utilized wheat immature embryo as explant tissue, MS medium, 1 mg/l 2,4-D for callus induction, 0.5 mg/l 2,4-D for callus maintenance, 0.1 mg/l 2,4-D for shoot formation, and no hormones for root formation.

This approach has also been described for barley. Orton et al., *Theor. Appl. Genet.* 57, 89 (1980) utilized immature embryos as explant tissue, modified MS medium containing 5 mg/l 2,4-D for callus induction, B5 medium containing 4 mg/l 2,4-D for callus maintenance, and MS medium containing no hormones for plant regeneration. Orton, *Environ. Exp. Bot.* 19, 319 (1979) describes a similar process using immature ovaries and B5 medium. The hormones were 2,4-D for callus induction and callus maintenance, and a mixture of $GA_3$ and kinetin for plant regeneration. Cheng et al., *Planta.* 123, 307 (1975) utilized apical meristems as the explant tissue, modified MS and Cheng medium, a mixture of IAA, 2,4-D and 2-isopentyladenine (2-ip) for callus induction, a mixture of IAA, 2-ip, and either 2,4-D, NAA or p-chlorophenoxyacetic acid for callus maintenance, and no hormones for plant regeneration.

In some instances, it is also possible to obtain plant regeneration from callus without transfer from the callus induction medium. Maddock et al., *J. Exp. Bot.* 34, 915 (1983) described that with certain genotypes of wheat, the medium utilized was suitable for callus induction and plant regeneration from immature embryos. The medium was MS and the hormone was a mixture of 2,4-D and coconut milk. The shoots with roots were cultured on MS medium for proliferation prior to transfer to soil. Kartel et al. describe callus induction and plant regeneration from mature embryos of barley on a B5 medium containing 2,4-D and kinetin.

The prior art does not describe a process for the regeneration of plants from most cereals that is widely applicable and further provides for excellent survival rate and recovery of regenerates. The present invention is the first instance of a broadly and generally applicable procedure for regenerating cereals which has a high survival rate and a high recovery of regenerates.

Cereal plants and seeds are produced by this process. The cereal plants resulting from this process may differ from the starting plant material as a result of somoclonal variation. The pathway is also useful in that it will enable the use of various selection processes to provide further variation. The plants which are produced can be used in conventional breeding programs.

SUMMARY OF THE INVENTION

The process of the present invention comprises the steps of inducing callus formation on an induction medium from tissue of a cereal plant, such as barley, corn, wheat, rice and sorghum, culturing the callus on a series of media to induce differentiation, and establishing the plantlet so that it will survive transplantation to soil. The series of media for inducing differentiation may comprise a single medium or it may comprise a sequence of two or more media. Upon differentiation, the callus forms shoots which form roots.

More specifically, the present process comprises the steps of:

(a) culturing tissue obtained from a cereal plant on an induction medium comprising mineral salts, vitamins, sucrose and a hormone in an amount sufficient to ensure callus formation, (b) culturing the callus on a series of media, said series comprising at least one medium and each medium comprises mineral salts, vitamins, sucrose and a hormone in an amount sufficient to insure differentiation to plantlets having shoots and roots at the completion of the series, and (c) culturing the plantlets on an establishment medium comprising mineral salts, vitamins and sucrose, whereby the plantlets are established so that they can be transplanted to soil.

The source of the tissue is preferably immature embryos from cultivars of barley (*Hordeum vulgare*), corn (*Zea mays*), wheat (*Triticum aestivium*), sorghum (*sorghum bicolor*), and mature seeds for cultivars of rice (*Oryza sativa*). The media preferably contain MS salts and the vitamins myo-insitol and thiamine. In the preferred embodiment, the series of media for differentiation comprises four different media having different hormones and functions.

BRIEF DESCRIPTION OF THE FIGURE

The FIGURE illustrates the various sequences which may be used to regenerate cereal plants according to the present process.

DETAILED DESCRIPTION OF THE INVENTION

Figure 1:
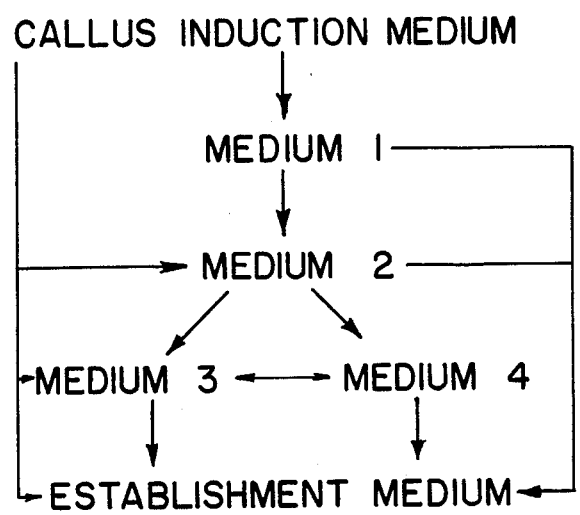

The present invention is directed to a process for regenerating cereals, especially barley, corn, wheat, rice and sorghum, through the use of cell or tissue culture. In this process, regenerated cereal plantlets are obtained which can be placed in soil and grown to maturation. The present invention is also directed to cereal plants obtained by the process and seeds obtained from these plants.

In general, the process comprises (a) culturing cereal plant tissue on a medium to produce calli, (b) culturing the calli on a series of media comprising at least one medium to produce plantlets, and (c) culturing the plantlets on a medium to develop them to the point where they can be transplanted to soil.

The plant tissue which is preferred for use in the initiation of callus is the immature embryo except for rice, where it is the mature seed. The plant tissue is isolated as follows for the individual cereals.

(a) barley—The immature embryos are isolated from seeds when they are in the range of 0.5-1.5 mm. The embryos are aseptically removed from the pericarps.

(b) corn—The immature embryos are isolated from the cob when they are in the range of 1.0-2.0 mm. The cob is harvested and surface sterilized. The embryos are isolated from each kernel.

(c) wheat—The immature embryos are isolated from seeds when they are in the range of 1.0-2.0 mm. The embryos are aseptically removed from the pericarps.

(d) rice—The mature seeds are harvested and surface sterilized.

(e) sorghum—The immature embryos are isolated from seeds when they are in the range of 0.5-1.5 mm. The embryos are aseptically removed from the pericarps.

The plant tissue are plated onto the callus induction medium.

The callus induction medium comprises mineral salts, vitamins and sucrose. The mineral salts comprise macroelements and microelements. The macroelements used in the induction medium may be the following compounds: magnesium sulfate, calcium chloride, monopotassium phosphate, potassium nitrate and ammonium nitrate. The microelements contained in this medium are: boric acid, manganese sulfate, zinc sulfate, sodium molybdate (VI), copper (II) sulfate, cobalt chloride, potassium iodide, iron (II) sulfate and disodium-ethylenediamine tetraacetic acid (EDTA). This combination of mineral salts is known in the art as the MS mineral salts. Other combinations of mineral salts may also be used as long as they do not adversely affect callus induction. Many combinations of mineral salts are known. These include, but are not limited to, N6, Heller, Nitsch and Nitsch, B5, and White.

The preferred amounts of the macroelements and microelements which are used to prepare one liter of medium are: 370 mg magnesium sulfate heptahydrate, 440 mg calcium chloride dihydrate, 170 mg monopotassium phosphate, 1900 mg potassium nitrate, 1650 mg ammonium nitrate, 6.2 mg boric acid, 16.9 mg manganese sulfate monohydrate, 8.6 mg zinc sulfate heptahydrate, 0.25 mg sodium molybdate (VI) dihydrate, 0.025 mg copper (II) sulfate pentahydrate, 0.025 mg cobalt chloride hexahydrate, 0.83 mg potassium iodide, 27.8 mg iron (II) sulfate heptahydrate, and 37.3 mg disodium-EDTA.

The callus induction medium further contains vitamins. The vitamins utilized are myo-inositol and thiamine. The preferred amounts of the vitamins used to prepare one liter of medium are 0.4 mg thiamine hydrochloride and 100 mg myo-inositol.

The induction medium contains 1-3% sucrose, preferably 2%, and a gelling agent such as agar or Gelrite TM (Kelco Commercial Development). It is preferred to use Gelrite TM at a concentration of 0.2%. The medium has a pH of 5.5-5.8 with a preferred pH of 5.8, and is sterilized by autoclaving.

In addition to the above components, the callus induction medium also contains a hormone. As used herein, hormone is intended to mean any natural or synthetic compound which has a regulatory affect on plants or plant tissues and any additive which may be combined with said compound. Plant hormones include auxins and cytokinins. Additives which may be included with auxins and cytokinins include coconut milk and casein hydrolysate.

It has been found that the hormone which is useful for callus induction may be selected from the group comprising 2,4-D, a mixture of 2,4-D and IAA, a mixture of 2,4-D, NAA and alpha-indole butyric acid (IBA) or a mixture of 2,4-D, IAA and NAA. Callus induction media containing these hormones will be referred to herein as callus induction medium A, B, C or D, respectively. The amount of hormone that is present is sufficient to insure callus formation. Generally, 1-4 mg/l 2,4-D; 1-4 mg/l 2,4-D and 1-2 mg/l IAA; 1-4 mg/l 2,4-D, 2-4 mg/l NAA and 2-4 mg/l IBA; or 1-4 mg/l 2,4-D, 1-2 mg/l IAA and 1-2 mg/l NAA is utilized as the hormone in the induction medium. It is preferred to use 1.0 mg/l 2,4-D; 3.0 mg/l 2,4-D and 2.0 mg/l IAA; 1.0 mg/l 2,4-D, 2.0 mg/l NAA and 2.0 mg/l IBA; or 4.0 mg/l 2,4-D, 1.0 mg/l IAA and 2.0 mg/l NAA. IAA is membrane filtered prior to the medium being autoclaved.

The plant tissue is plated on the callus induction medium and cultured in diffused light with a photoperiod of 16 hours for, two-three weeks for barley, corn and wheat, preferably, 15 days for barley, 21 days for corn, 20 days for wheat, and four-five weeks, preferably 30 days for rice and sorghum. During this time the embryo undergoes dedifferentiation and callus formation. It is preferred to use callus induction medium C for callus formation with each cereal.

After culturing the plant tissue on the callus induction medium, the callus is cultured on a series of media to ensure differentiation. The series of media comprises at least one medium. If more than one medium are utilized, each is different. When only one medium is utilized, it may be the same medium as for callus induction or it may be a different medium from this one. The callus induction medium is used for differentiation only when the callus undergoes differentiation during the culture time for inducing callus. This is more likely to occur on media A and B than on media D and C. As used herein, differentiation medium will refer to any medium which is employed in the series of media for differentiation. It is to be understood that differentiation does not necessarily occur on each medium utilized. That is, a particular medium utilized in this series may be used to enhance callus proliferation or to loosen a mass of embryoids. However, differentiation does occur after culturing on the series.

The various pathways that may be utilized in the series of media for differentiation is illustrated in the FIGURE. As used herein, medium 1, 2, 3 and 4, as well as the callus induction medium, comprise the series of media for differentiation. When the callus induction medium is A, B, C or D, the callus can be transferred to medium 1. After culturing on medium 1, the callus is transferred to medium 2. After culturing on medium 2, the callus can be transferred to either medium 3, medium 4, and the plants can be transferred to the establishment medium. After culturing on medium 3 or 4, the differentiating callus can be transferred to medium 4 or 3, respectively, and the plants can be transferred to the establishment medium. Callus can be transferred back and forth between medium 3 and medium 4 as necessary. The callus can also be transferred to medium 2 or to medium 3 directly. This is more likely to occur when callus induction medium A or B is used than when callus induction medium D or C is used. In addition, sometimes a callus will undergo differentiation on the callus induction medium after the callus had formed and during the culture time utilized. In this case, the plantlets are transferred to the establishment medium directly. In the preferred embodiment, the media sequencing is: callus induction medium (A, B, C or D)—medium 1—medium 2—medium 3—medium 4—establishment medium.

The length of time that culturing occurs on each medium, when utilized in any pathway, is as described for the callus induction medium.

Each medium utilized in the series of media for differentiation comprises mineral salts, vitamins, sucrose and a hormone. The mineral salts, vitamins and sucrose are the same for each of media 1, 2, 3 and 4, and only the hormone differs among them. It is the combination of hormones and media sequence which insures the differentiation of the callus to plantlets during the series of media for differentiation. The mineral salts, vitamins and sucrose in each medium are the same as previously described for the callus induction medium. Each medium is solidified using agar or Gelrite TM, preferably 0.2% Gelrite TM, as the gelling substance. Each medium has a pH of 5.5-5.8, preferably 5.8 and is sterilized by autoclaving.

As described above, media 1, 2, 3 and 4 have different hormones. The hormone used in each of these media are shown in the following table:

| Medium | Component | HORMONE Amount (mg/l) general | preferred |
|---|---|---|---|
| 1 | 2,4-D | 0.7-1 | 1 |
|   | coconut milk | 5-15% | 10% |
| 2 | IBA | 2-5 | 5 |
|   | BA | 0.1-0.5 | 0.1 |
| 3 | 2,4-D | 0.1-0.2 | 0.1-0.2 |
|   | $GA_3$ | 0.35-1.0 | 0.35 |
|   | BA | 0.1-0.5 | 0.1 |
|   | coconut milk | 5-15% | 0-10% |
| 4 | 2,4-D | 0.1-0.5 | 0.5 |
|   | BA | 0.1-0.5 | 0.1 |
|   | coconut milk | 5-15% | 0-10% |

The most preferred hormone make-up of medium 3 is 0.2 mg/l 2,4-D, 0.35 mg/l $GA_3$, 0.1 mg/l BA and 10% coconut milk. $GA_3$ is sterilized by membrane filtration prior to the medium being autoclaved.

Each of the media used in the series of media for differentiation has a specific function. Medium 1 serves to enhance proliferation of embryogenic callus tissue and sustain donor tissue. The coconut milk is important for this latter function. Medium 2 separates embryogenic tissue to a loose mass to avoid fusion of tissue and reduces 2,4-D carryover either to promote differentiation of somatic embryoids or to promote shoot and root formation, i.e. morphogenesis of the callus. Medium 3 releases control on differentiation and promotes shoot and root formation from somatic embryoids. Medium 4 promotes differentiation to shoots and roots from morphogenic callus. In addition, media 3 and 4 maintain and mature latent embryogenic tissue to form plantlets. In addition, in certain circumstances the callus induction medium can promote plantlet formation after the auxin level has been reduced as a result of callus growth.

As discussed above, each medium in the series of media for differentiation has a particular function. The transfer of material from one medium to another medium in the sequence depends on type of tissue that has developed on the first medium and the desired objective of proceeding with that tissue. When plantlets, i.e. callus containing shoots and roots, are obtained, they are transferred to the establishment medium. If tissue becomes a disorganized mass of callus with a potential of entering a structural differentiation, this tissue is transferred to medium 1. Medium 1 will then tend to extend the growth of the disorganized structures and stimulate further embryogenic tissue development. When distinct structures arise within the tissue, the tissue is transferred to medium 2 which helps to segregate the embryogenic tissue to more distinctly structured mass and to enhance differentiation of embryoids or morphogenic structures. Embryoids per se or tissues containing a great extent of embryoids are transferred to medium 3 for shoot and root formations from the embryoids. Tissue containing primarily morphogenic structures or embryogenic callus will be transferred to medium 4 for the formation of shoots and roots from the morphogenic structures and to promote embryoid development. Once embryoids have been exhausted from the tissue transferred to medium 3, the tissue can then be transferred to medium 4 to further enhance the morphogenic response. Similarly, once the morphogenic structures and embryogenic callus is exhausted from the tissue on medium 4, the tissue can be transferred to medium 3 for embryoid differentiation. Whenever transfers are occurring between media 3 and 4, it is understood herein that the plantlets which have been formed are first removed and plated on the establishment medium. By utilizing this procedure, the number of plants which is obtained from each embryo or seed is optimized.

After culturing on the series of media for differentiation, the differentiated material, i.e., plantlets having shoots and roots, is transferred to an establishment medium. The establishment medium contains the same mineral salts and vitamins as the callus induction medium. It further contains sucrose in the same amount as the callus induction medium, i.e., 1-2%, preferably 2%. The establishment medium has a pH of 5.5-5.8, preferably 5.8, and is sterilized as described above. Gelrite TM, preferably 0.2%, or agar is used to solidify the medium.

After culturing the plantlets on the establishment medium for 7-21 days, preferably 10-15 days, in diffused light with a photoperiod of 16 hours per day, the plantlets are transferred to the soil. The plantlets are removed and the Gelrite TM is washed off. The plantlets are then planted in a mixture of one part potting soil and two parts perlite. After three weeks, the plants are transplanted to a mixture of one part potting soil and one part perlite.

This process is useful for regenerating plantlets from tissue of many cultivats of cereals.

The present invention will be further described by reference to the following non-limiting examples. In these examples, culturing in the light refers to culturing in diffused light having a photoperiod of 16 hours per day at 23°-25° C. unless indicated otherwise. The temperature during the 8 hours dark phase is 21°-23° unless indicated otherwise. Although the entire sequences are described in the regeneration examples, plantlets were transferred to the establishment medium once they were formed.

EXAMPLE 1

Preparation of Solutions

The following stock solutions or solutions were prepared for use in making the medium described in further detail below.

1. Mineral Salts and Vitamins

The solution was prepared immediately before use by dissolving one packet of Murashige minimal organics medium without sucrose (Gibco Laboratories Catalog No. 510-3118) in 800 ml of distilled, deionized water. A small amount of the water was used to rinse out the packet. The packet includes a pH buffering agent.

2. Hormones (A) A 0.1 mg/ml stock solution of 2,4-D was prepared by dissolving 10 mg of 2,4-D in 20 ml of 70% ethanol and diluting to 100 ml with distilled, deionized water.

(B) A 0.1 mg/ml stock solution of IAA was prepared by dissolving 10 mg of IAA in 20 ml of 70% ethanol and diluting to 100 ml with distilled, deionized water. 10 ml aliquots were stored frozen in vials wrapped in aluminum foil.

(C) A 0.1 mg/ml stock solution of IBA was prepared as described for 2,4-D.

(D) A 0.1 mg/ml stock solution of NAA was prepared as described for 2,4-D.

(E) A 0.1 mg/ml stock solution of $GA_3$ was prepared as described for 2,4-D.

(F) A 0.1 mg/ml stock solution of BA was prepared by dissolving 10 mg of BA in 10 ml of 0.5N HCl and diluting to 100 ml with distilled, deionized water.

(G) Coconut milk was prepared by decanting endosperm liquid from a coconut. The average volume of endosperm liquid is 100 ml. The liquid was heated to 90° C. for 3-5 minutes to precipitate protein and cooled to room temperature. The liquid was then filtered through Watman #3 filter paper and suction filtered through a 47 mm Gelman glass fiber filter. The filtrate was stored frozen until used.

EXAMPLE 2

Preparation of Media

1. Callus Induction Medium (A) Callus Induction Medium A. Callus induction medium A was prepared by adding 20 g of sucrose and 10 ml of the 2,4-D stock solution to the mineral salts and vitamins solution, 2 g of Gelrite TM was added and the volume brought to one liter with distilled, deionized water. The medium was then autoclaved for 20 minutes at 15 psi. The cooling medium was poured into petri dishes.

To prepare medium A having a different concentration of 2,4-D, the appropriate amount of the 2,4-D stock solution was added. For example, to prepare medium A having a concentration of 2.0 mg/l 2,4-D, 20 ml of the stock solution was used.

(B) Callus Induction Medium B. Callus induction medium B was prepared as described for medium A, except that (a) 30 ml of the 2,4-D stock solution was utilized, and (b) 20 ml of the IAA stock solution was sterilized by filtering through a 0.22 micron membrane and added to the cooling solution (35° C.). To prepare medium B having different concentrations of 2,4-D and IAA, the appropriate amounts of the 2,4-D and IAA stock solutions were added as described above.

(C) Callus Induction Medium C. Callus induction medium C was prepared as described for medium A, except that 30 ml of the 2,4-D stock solution, 20 ml of the NAA stock solution and 20 ml of the IBA stock solution were utilized in place of the 2,4-D stock solution of medium A. Medium C having different concentrations of 2,4-D, NAA and IBA was prepared as described above using the appropriate amounts of the hormone stock solutions.

(D) Callus Induction Medium D. Callus induction medium D was prepared as described for medium B, except that (a) 40 ml of the 2,4-D stock solution and 20 ml of the NAA stock solution were used in place of the 2,4-D stock solution of medium B, and (b) only 10 ml of the IAA stock solution was utilized.

2. Series of Media for Differentiation (A) Medium 1. Medium 1 was prepared by adding 20 g of sucrose, 10 ml of the 2,4-D stock solution and 100 ml of coconut milk were added to the solution of mineral salts and vitamins. 2 g of Gelrite ™ was added and the volume brought to one liter. The medium was autoclaved for 20 minutes at 15 psi and poured into petri dishes. To prepare medium 1 with different concentrations of 2,4-D and coconut milk, the appropriate amounts of the stock solutions are added in the manner previously described.

(B) Medium 2. Medium 2 was prepared as described for medium 1, except that 50 ml of the IBA stock solution and 1 ml of the BA stock solution were utilized in place of 2,4-D and coconut milk. Medium 2 having different concentrations of IBA and BA was prepared in an analogous manner as described for other media.

(C) Medium 3. Medium 3 was prepared as described for medium 1, except that (a) 2 ml of the stock solution of 2,4-D was used, (b) 1 ml of the stock solution of BA was added to the solution when 2,4-D and coconut milk were added, and (c) 3.5 ml of the GA$_3$ stock solution was sterilized by filtering through a 0.22 micro membrane and added to the cooling solution (35° C.). To prepare medium 3 having different concentrations of hormones, the appropriate amounts of the 2,4-D, GA$_3$, BA and coconut milk stock solutions were utilized.

(D) Medium 4. Medium 4 was prepared as described for medium 1, except that (a) 5 ml of the 2,4-D stock solution was used, and (b) 1 ml of the stock solution of BA was added to the solution when 2,4-D and coconut milk were added. Medium 4 having different concentrations of 2,4-D BA and coconut milk was prepared in an analogous manner as described for other media.

3. Establishment Medium

The establishment medium was prepared by adding 20 g of sucrose to the mineral salts and vitamins solution. 2 g of Gelrite ™ was then added and the volume brought to one liter. The medium was autoclaved for 20 minutes at 15 psi and poured into petri dishes.

EXAMPLE 3

Barley Regeneration

Immature embryos were isolated from seeds of the barley *Hordeum vulgare* cv. Clark when they were 0.5-1.5 mm in length. Seeds were wiped with 70% ethanol and the embryos were aseptically removed from the pericarps and plated on callus induction medium C contained in a petri dish. Medium C was prepared as described in the preceding example, using 3 mg/l 2,4-D, 2 mg/l NAA, and 2 mg/l IBA. The petri dish was placed in the light and cultured 15 days to form calli.

At that time each callus was transferred to medium 1, which was prepared as described above using 1 mg/l 2,4-D and 10% coconut milk, and also contained in a petri dish. The callus was cultured on this medium in the light for 15 days for proliferation of embryogenic callus.

Each callus was then transferred to medium 2. Medium 2 was prepared as described in Example 2, and contained 2 mg/l IBA and 0.1 mg/l BA. The callus was cultured on this medium for 15 days in the light to promote differentiation of somatic embryoids.

At this time, each callus was transferred to medium 4 containing 0.5 mg/l 2,4-D and 0.1 mg/l BA prepared as described in the preceding example. The callus was cultured 15 days in the light for shoot formation.

Callus with shoots was then transferred to medium 3 containing 0.1 mg/l 2,4-D, 0.35 mg/l GA$_3$, and 0.1 mg/l BA prepared as described above. Culturing was conducted for 15 days in the light for root development.

At that time, the plantlets were transferred to the establishment medium prepared as described in Example 2. After 15 days, the plantlets were transferred to soil. The plantlets were removed from the flasks and the Gelrite ™ was washed off thoroughly using tap water. The plantlets were planted in potting cubes containing one part potting soil and two parts perlite and watered twice weekly for three weeks. The plants were then planted in 10" pots containing one part potting soil and one part perlite. The plants were watered three times per week and fertilized bi-weekly.

EXAMPLE 4

Barley Regeneration

Immature embryos were isolated from seeds of the barley *Hordeum vulgare* cv. Morex as described in Example 3. The embryos were plated onto callus induction medium A containing 1 mg/l 2,4-D and cultured in the light for 15 days. Each callus was then transferred to medium 2 containing 5 mg/l IBA and 0.1 mg/l BA. After culturing in the light for 15 days, each callus was transferred to medium 4 containing 0.5 mg/l 2,4-D, 0.1mg/l BA and 10% coconut milk. Each callus was cultured on medium 4 for 15 days in the light at which time the plantlets were transferred to the establishment medium. The plantlets were then handled as described in Example 3. 95 plants were produced from three immature embryos.

EXAMPLE 5

Corn Regeneration

Immature embryos were isolated from a cob of the corn *Zea mays* A641 when they were 1.0–2.0 mm in length. The cob was surface sterilized in a 20% bleach solution for 20 minutes and rinsed twice in 500 ml of sterile water. The embryos were then removed from each kernel and plated onto callus induction medium C with the embryo axis in contact with the medium. Medium C was prepared as described in Example 2, containing 3 mg/l 2,4-D, 2 mg/l NAA, and 2 mg/l IBA. Culturing was conducted in the light for 21 days to form calli.

At that time, each callus was transferred to medium 1 containing 1 mg/l 2,4-D and 10% coconut milk prepared as described above. The callus was cultured on this medium for 21 days in the light.

Each callus was then transferred to medium 2 containing 5 mg/l IBA and 0.1 mg/l BA prepared as previously described. Culturing was conducted in the light for 21 days.

Each callus with shoots and roots was then transferred to the establishment medium and cultured in the light for 21 days before being transferred to soil as described in Example 3.

This procedure was also followed for immature embryos isolated from *Zea mays* Cshbz-m 4Wx,NoAc, 820262x *Zea mays* CDsshbz-m4, Ac, 800328A-7xAl, and *Zea mays* B73. Plants were obtained from eacy variety, except the latter.

EXAMPLE 6

Corn Regeneration

Immature embryos were isolated from the cultivars of corn identified in Example 5 as previously described. The embryos were plated onto callus induction medium C and cultured in the light for 21 days as described in Example 5.

At that time, each callus was transferred to medium 3 containing 0.2 mg/l 2,4-D, 0.35 mg/l GA$_3$, 0.1 mg/l BA and 10% coconut milk, and cultured in the light for 21 days.

The callus with shoots and roots were then transferred to establishment medium and cultured in the light for 21 days before being transferred to soil as described in Example 3. Plants were obtained from each cultivar except *Zea mays* B73.

EXAMPLE 7

Corn Regeneration

Immature embryos were isolated from the cultivars of corn identified in Example 5 as previously described. The embryos were plated onto callus induction medium C and cultured in the light for 21 days as described in Example 5.

The callus were then transferred to establishment medium and cultured in the light for 21 days before being transferred to soil as described in Example 3. Plants were obtained from each cultivar except *Zea mays* B73.

EXAMPLE 8

Wheat Regeneration

Immature embryos were isolated from seeds of the wheat *Triticum aestivium* S-5704 (CIMMYT 1981) when they were 1.0–2.0 mm in length, in the same procedure as described for barley in Example 3. The embryos were plated onto callus induction medium C having 3 mg/l 2,4-D, 2 mg/l NAA and 2 mg/l IBA, and cultured in the light for 20 days.

At that time, each callus was transferred in the same sequence as described for corn in Example 5, except that transfer times were 20 days. That is, the sequence was medium 1, medium 2, and establishment medium. Plants were transferred to soil as described in Example 3 after three days.

This procedure was repeated for immature embryos isolated from *Triticum aestivium* S-5829 (CIMMYT 1981) and *Triticum aestivium* S-6006 (CIMMYT 1981). Plants were obtained in each instance.

EXAMPLE 9

Wheat Regeneration

Immature embryos were isolated from the cultivars of wheat identified in Example 8, as previously described. The embryos were plated onto callus induction medium C and cultured in the light for 21 days, as described in Example 8.

At that time, each callus was transferred to medium 1 containing 1 mg/l 2,4-D and 10% coconut milk, and cultured in the light for 20 days. The callus was then transferred to the establishment medium and cultured for 15 days in the light before being transferred to the soil, as described in Example 3. Plants were obtained from each cultivar.

EXAMPLE 10

Wheat Regeneration

Immature embryos were isolated from the cultivars of wheat identified in Example 8, as previously described. The embryos were plated onto callus induction medium A containing 1 mg/l 2,4-D, and cultured in the light for 20 days.

At that time, each callus was transferred to medium 1 containing 1 mg/l 2,4-D and 10% coconut milk, and cultured in the light for 20 days. Each callus was then transferred to medium 3 containing 0.2 mg/l 2,4-D, 0.35 mg/l GA$_3$, 0.1 mg/l BA and 10% coconut milk. After culturing for 20 days in the light, plants were obtained which can be transferred to establishment medium and then to soil.

EXAMPLE 11

Rice Regeneration

Mature seeds were obtained from the rice *Oryza sativa* M9 or CSM7, each obtained from Rice Growers Association of California, and sterilized in a solution of 70% ethanol containing one drop of Liquinox ® detergent for one minute, and then in a solution of 50% bleach containing one drop of Liquinox ® for 15 minutes. The seeds were rinsed twice in 500 ml of sterile water and plated onto callus induction medium C containing 3 mg/l 2,4-D, 2 mg/l NAA and 2 mg/l IBA. Culturing was conducted for 30 days in the light.

At that time, each callus was transferred to medium 1 containing 1 mg/l 2,4-D and 10% coconut milk and cultured for 30 days in the light. Each callus was then transferred to medium 4 containing 0.5 mg/l 2,4-D, 0.1 mg/l BA and 10% coconut milk. The callus were then cultured for 30 days in the light, before being transferred to the establishment medium. Plants have been obtained in each instance.

EXAMPLE 12

Sorghum Regeneration

Immature embryos were isolated from seeds of the sorghum *Sorghum bicolor* NP3 obtained from U.S. Department of Agriculture (University of Nebraska) when they were 0.5-1.5 mm in length, in the same procedure as described for barley in Example 3. The embryos were plated onto callus induction medium C having 3 mg/l 2,4-D, 2 mg/l NAA and 2 mg/l IBA, and cultured in the light for 30 days.

At that time, each callus was transferred to medium 1 containing 1 mg/l 2,4-D and 10% coconut milk, and cultured in the light for 30 days. Each callus was then transferred to either (a) establishment medium, (b) medium 4 containing 0.5 mg/l 2,4-D, 0.1 mg/l BA and 10% coconut milk; or (c) medium 3 containing 0.2 mg/l 2,4-D, 0.35 mg/l $GA_3$, 0.1 mg/l BA and 10% coconut milk. Shoots have been obtained in each instance.

EXAMPLE 13

Barley Regeneration

Immature embryos were isolated from seeds of the barley *Hordeum vulgare* cv. Prioline as described in Example 3 and plated onto callus induction medium A containing 1 mg/l 2,4-D. After culturing in the light for 15 days, each callus was transferred to medium 1 containing 1 mg/l 2,4-D and 10% coconut milk and cultured in the light for 15 days. The callus was then transferred to medium 2 containing 5 mg/l IBA and 0.1 mg/l BA and cultured for 15 days in the light. Each plantlet was then transferred to establishment medium and handled as described in Example 3. 78 plants were produced from 3 embryos.

EXAMPLE 14

Barley Regeneration

Immature embryos were isolated from seeds of the barley *Hordeum vulgare* cv. Andre and plated onto callus induction medium A as described in Example 13. Each plantlet that differentiated from the callus which formed on this medium was transferred to the establishment medium and handled as described in Example 3. 159 plants were produced from 5 embryos.

EXAMPLE 15

Barley Regeneration

Immature embryos were isolated from seeds of the barley *Hordeum vulgare* cv. Clark and plated on callus induction medium C as described in Example 3. The embryos were cultured on this medium and transferred to medium 1 as described in Example 3. After 15 days of culturing in the light, the callus was transferred to medium 2, containing 5 mg/l IBA and 0.1 mg/l BA and cultured in the light for 15 days. The plantlets were then transferred to the establishment medium and handled as described in Example 3. 114 plants were obtained from 7 embryos.

EXAMPLE 16

Barley Regeneration

An immature embryo was isolated and plated on callus induction medium C as described in Example 15. The callus was transferred to medium 3 after culturing 15 days in the light. After a further 15 days culturing in the light, plantlets were transferred to the establishment medium and handles as described in Example 3. 67 plants were obtained from this embryo.

EXAMPLE 17

Barley Regeneration

Immature embryos were isolated as described in Example 15 and plated on callus induction medium B containing 3 mg/l 2,4-D and 2 mg/l IAA. After culturing in the light for 15 days, each callus was transferred to medium 1 and the sequence followed as described in Example 15. 26.9 plants per embryo were obtained.

EXAMPLE 18

Barley Regeneration

Immature embryos were isolated and plated on callus induction medium A as described in Example 14. After culturing for 15 days in the light, each callus was transferred to medium 1 containing 1 mg/l 2,4-D and 10% coconut milk. The plantlets were transferred to the establishment medium after 15 days and handled as described in Example 3. 19 plants were obtained per embryo.

EXAMPLE 19

Barley Regeneration

Immature embryos were isolated, plated on callus induction medium C and cultured as described in Example 15. The callus was then transferred to medium 2 containing 5 mg/l IBA and 0.1 mg/l BA and cultured for 15 days in the light. The plantlets were then transferred to the establishment medium and handled as described in Example 3. 23 plants per embryo were obtained.

EXAMPLE 20

Barley Regeneration

Immature embryos were isolated as described in Example 15 and planted on callus induction medium D containing 4 mg/l 2,4-D, 1 mg/l IAA and 2 mg/l NAA. The embryos were cultured in the light for 15 days after which each callus was transferred to medium 2 and handled as described in Example 19. 35.3 plants were obtained per embryo plated.

While the invention has been described in connection with specific embodiments thereof, it will be understood that it is capable of further modifications. This application is intended to cover any variations, uses or adaptations of the invention following, in general, the principles of the invention and including such departures from the present disclosure as come within known and customary practice within the art to which the invention pertains.

What is claimed is:

1. A process for regenerating cereal plantlets from cell or tissue culture which comprises the steps of:
    (a) culturing tissue obtained from a cereal plant selected from the group consisting of barley, corn which is capable of being regenerated on medium containing 2,4-D, wheat, rice and sorghum on a callus induction medium comprising mineral salts, vitamins, sucrose and a hormone selected from the group consisting of (A) 2,4-D, (B) a mixture of 2,4-D and IAA, (C) a mixture of 2,4-D, NAA and IBA, and (D) a mixture of 2,4-D, IAA and NAA, in an amount sufficient to insure callus formation;

(b) culturing said callus on a series of media for differentiation, said series comprises utilizing one to four media selected from the group consisting of medium 1, medium 2, medium 3, medium 4 and medium 5, each medium comprises mineral salts, vitamins, sucrose and a hormone in an amount sufficient to insure differentiation to plantlets having shoots and roots after culturing on said series, said hormone of medium 1 comprising 2,4-D and coconut milk, of medium 2 comprising IBA and BA, of medium 3 comprising 2,4-D, GA$_3$, BA and coconut milk, of medium 4 comprising 2,4-D, BA and coconut milk, and of medium 5 comprising the hormone of said callus induction medium, with the proviso that medium 5 alone is not said series when the tissue is from wheat or corn wherein medium 1 is capable of enhancing proliferation of embryogenic callus tissue and sustaining donor tissue, medium 2 is capable of separating embryogenic tissue into a loose mass and enhancing differentiation of somatic embryoids or morphogenic structures, medium 3 is capable of promoting shoot and root formation from somatic embryoids, medium 4 is capable of promoting differentiation to shoots and roots from morphogenic callus and medium 5 is capable of promoting plantlet formation; and (c) culturing said plantlets on an establishment medium comprising mineral salts, vitamins and sucrose, whereby plants are obtained capable of growth in soil.

2. The process of claim 1 wherein said tissue is obtained from immature embryo for barley, corn, wheat and sorghum, and from mature seeds for rice.

3. The process of claim 1 wherein the concentrations of said hormones are:

(1) (A) 1–4 mg/l 2,4-D, (B) 1–4 mg/l 2,4-D and 1–2 mg/l IAA, (C) 1–4 mg/l 2,4-D, 2–4 mg/l NAA and 2–4 mg/l IBA and (D) 1–4 mg/l 2,4-D, 1–2 mg/l IAA and 1–2 mg/l NAA in said callus induction medium;

(2) 0.7–1.0 mg/l 2,4-D and 5–15% coconut milk in said medium 1;

(3) 2–5 mg/l IBA and 0.1–0.5 mg/l BA in said medium 2;

(4) 0.1–0.2 mg/l 2,4-D, 0.35–1.0 mg/l GA$_3$, 0.1–0.5 mg/l BA and 5–15% coconut milk in said medium 3; and (5) 0.1–0.5 mg/l 2,4-D, 0.1–0.5 mg/l BA and 5–15% coconut milk in said medium 4.

4. The process of claim 3 wherein the concentration of sucrose is 1–3% in the callus induction medium and the series of media for differentiation and 1–2% in the establishment medium.

5. The process of claim 4 wherein said mineral salts of all media are magnesium sulfate, calcium chloride, monopotassium phosphate, potassium nitrate, ammonium nitrate, boric acid, manganese sulfate, zinc sulfate, sodium molybdate (VI), copper (II) sulfate, cobalt chloride, potassium iodide, iron (II) sulfate and disodium-EDTA.

6. The process of claim 5 wherein said mineral salts are the MS salts.

7. The process of claim 4 wherein said vitamins comprise myo-inositol and thiamine.

8. The process of claim 4 wherein said medium 5 is callus induction medium having a reduced auxin level caused by callus growth.

9. The process of claim 4 wherein said series comprises in sequence medium 1, medium 2, medium 3 and medium 4.

10. The process of claim 4 wherein said series comprises in sequence medium 1 and medium 2.

11. The process of claim 4 wherein said series comprises in sequence medium 1, medium 2 and medium 3.

12. The process of claim 4 wherein said series comprises in sequence medium 1, medium 2 and medium 4.

13. The process of claim 1 wherein said series comprises in sequence medium 1, medium 2, medium 4 and medium 3.

14. The process of claim 4 wherein said series comprises medium 3.

15. The process of claim 4 wherein said series comprises in sequence medium 3 and medium 4.

16. A process for regenerating cereal plantlets from cell or tissue culture which comprises the steps of:

(a) culturing tissue obtained from a cereal plant selected from the group consisting of barley, corn which is capable of being regenerated on medium containing 2,4-D, wheat, rice and sorghum on a callus induction medium comprising mineral salts comprising magnesium sulfate, calcium chloride, monopotassium phosphate, potassium nitrate, ammonium nitrate, boric acid, manganese sulfate, zinc sulfate, sodium molybdate (VI), copper (II) sulfate, cobalt chloride, potassium iodide, iron (II) sulfate and disodium-EDTA; vitamins comprising myo-inositol and thiamine; sucrose and a hormone selected from the group consisting of (A) 2,4-D, (B) a mixture of 2,4-D and IAA, (C) a mixture of 2,4-D, NAA and IBA, and (D) a mixture of 2,4-D, IAA and NAA, in an amount sufficient to insure callus formation;

(b) culturing said callus on a series of media for differentiation, said series comprises utilizing one to four media selected from the group consisting of medium 1, medium 2, medium 3, medium 4 and medium 5, each medium comprises mineral salts comprising magnesium sulfate, calcium chloride, monopotassium phosphate, potassium nitrate, ammonium nitrate, boric acid, manganese sulfate, zinc sulfate, sodium molybdate (VI), copper (II) sulfate, cobalt chloride, potassium iodide, iron (II) sulfate and disodium-EDTA; vitamins comprising myo-inositol and thiamine; sucrose and a hormone in an amount sufficient to insure differentiation to plantlets having shoots and roots after culturing on said series, said hormone of medium 1 comprising 2,4-D and coconut milk, of medium 2 comprising IBA and BA, of medium 3 comprising 2,4-D, GA$_3$, BA and coconut milk, of medium 4 comprising 2,4-D, BA and coconut milk, and of medium 5 comprising the hormone of said callus induction medium, with the proviso that medium 5 alone is not said series when the tissue is from wheat or corn wherein medium 1 is capable of enhancing proliferation of embryogenic callus tissue and sustaining donor tissue, medium 2 is capable of separating embryogenic tissue into a loose mass and enhancing differentiation of somatic embryoids or morphogenic structures, medium 3 is capable of promoting shoot and root formation from somatic embryoids, medium 4 is capable of promoting differentiation to shoots and roots from morphogenic callus and medium 5 is capable of promoting plantlet formation; and (c) culturing said plantlets on an establishment medium comprising mineral salts comprising magnesium sulfate, calcium chloride, monopotassium phosphate, potassium nitrate, ammonium nitrate, boric acid, manganese sulfate, zinc sulfate, sodium molybdate (VI), copper (II) sulfate, cobalt chloride, potassium iodide, iron (II) sulfate and disodium-EDTA; vitamins comprising myo-inositol and thiamine; and sucrose, whereby plants are obtained capable of growth in soil.

17. The process of claim 16 wherein said tissue is obtained from immature embryo of barley, corn, wheat and sorghum, and from mature seeds of rice.

18. The process of claim 16 wherein the concentrations of said hormones are:
(1) (A) 1–4 mg/l 2,4-D, (B) 1–4 mg/l 2,4-D and 1–2 mg/l IAA, (C) 1–4 mg/l 2,4-D, 2–4 mg/l NAA and 2–4 mg/l IBA and (D) 1–4 mg/l 2,4-D, 1–2 mg/l IAA and 1–2 mg/l NAA in said callus induction medium;
(2) 0.7–1.0 mg/l 2,4-D and 5–15% coconut milk in said medium 1;
(3) 2–5 mg/l IBA and 0.1–0.5 mg/l BA in said medium 2;
(4) 0.1–0.2 mg/l 2,4-D, 0.35–1.0 mg/l $GA_3$, 0.1–0.5 mg/l BA and 5–15% coconut milk in said medium 3; and
(5) 0.1–0.5 mg/l 2,4-D, 0.1–0.5 mg/l BA and 5–15% coconut milk in said medium 4.

19. The process of claim 18 wherein the concentration of sucrose is 1–3% in the callus induction medium and the series of media for differentiation and 1–2% in the establishment medium.

20. The process of claim 19 wherein said mineral salts are the MS salts.

21. The process of claim 19 wherein said medium 5 is callus induction medium having a reduced auxin level caused by callus growth.

22. The process of claim 19 wherein said series comprises in sequence medium 1, medium 2, medium 3 and medium 4.

23. The process of claim 19 wherein said series comprises in sequence medium 1 and medium 2.

24. The process of claim 19 wherein said series comprises in sequence medium 1, medium 2 and medium 3.

25. The process of claim 19 wherein said series comprises in sequence medium 1, medium 2 and medium 4.

26. The process of claim 19 wherein said series comprises in sequence medium 1, medium 2, medium 4 and medium 3.

27. The process of claim 19 wherein said series comprises medium 3.

28. The process of claim 19 wherein said series comprises in sequence medium 3 and medium 4.

29. A process for regenerating cereal plantlets from cell or tissue culture which comprises the steps of:
(a) culturing tissue obtained from a cereal plant selected from the group consisting of barley, corn which is capable of being regenerated on medium containing 2,4-D, wheat, rice and sorghum on a callus induction medium comprising MS mineral salts, vitamins comprising myo-inositol and thiamine; sucrose and a hormone selected from the group consisting of (A) 1–4 mg/l 2,4-D, (B) a mixture of 1–4 mg/l 2,4-D and 1–2 mg/l IAA, (C) a mixture of 1–4 mg/l 2,4-D, 2–4 mg/l NAA and 2–4 mg/l IBA, and (D) a mixture of 1–4 mg/l 2,4-D, 1–2 mg/l IAA and 1–2 mg/l NAA, in an amount sufficient to insure callus formation;
(b) culturing said callus on a series of media for differentiation, said series comprises utilizing one to four media selected from the group consisting of medium 1, medium 2, medium 3, medium 4 and medium 5, each medium comprises MS mineral salts, vitamins comprising myo-inositol and thiamine; sucrose and a hormone in an amount sufficient to insure differentiation to plantlets having shoots and roots after culturing on said series, said hormone of medium 1 comprising 0.7–1.0 mg/l 2,4-D and 5–15% coconut milk, of medium 2 comprising 2–5 mg/l IBA and 0.1–0.5 mg/l BA, of medium 3 comprising 0.1–0.5 mg/l 2,4-D, 0.35–1.0 mg/l $GA_3$, 0.5 mg/l BA and 5–15% coconut milk, of medium 4 comprising 0.1–0.5 mg/l 2,4-D, 0.1–0.5 mg/l BA and 5–15% coconut milk, and of medium 5 comprising the hormone of said callus induction medium, with the proviso that medium 5 alone is not said series when the tissue is from wheat or corn wherein medium 1 is capable of enhancing proliferation of embryogenic callus tissue and sustaining donor tissue, medium 2 is capable of separating embryogenic tissue into a loose mass and enhancing differentiation of somatic embryoids or morphogenic structures, medium 3 is capable of promoting shoot and root formation from somatic embryoids, medium 4 is capable of promoting differentiation to shoots and roots from morphogenic callus and medium 5 is capable of promoting plantlet formation; and
(c) culturing said plantlets on an establishment medium comprising MS mineral salts; vitamins comprising myo-inositol and thiamine; and sucrose, whereby plants are obtained capable of growth in soil.

30. The process of claim 29 wherein said tissue is obtained from immature embryo of barley, corn, wheat and sorghum, and from mature seeds of rice.

31. The process of claim 29 wherein the concentrations of said hormones are:
(1) (A) 1 mg/l 2,4-D, (B) 3 mg/l 2,4-D and 2 mg/l IAA, (C) 1 mg/l 2,4-D, 2 mg/l NAA and 2 mg/l IBA, and (D) 4 mg/l 2,4-D, 1 mg/l IAA and 2 mg/l NAA in said callus induction medium;
(2) 1 mg/l 2,4-D and 10% coconut milk in said medium 1;
(3) 5 mg/l IBA and 0.1 mg/l BA in said medium 2;
(4) 0.2 mg/l 2,4-D, 0.35 mg/l $GA_3$, 0.1 mg/l BA and 10% coconut milk in said medium 3; and
(5) 0.5 mg/l 2,4-D, 0.1 mg/l BA and 10% coconut milk in said medium 4.

32. The process of claim 31 wherein said said sucrose concentration is 2% in all media.

33. The process of claim 32 wherein said medium 5 is callus induction medium having a reduced auxin level caused by callus growth.

34. The process of claim 32 wherein said series comprises in sequence medium 1, medium 2, medium 3 and medium 4.

35. The process of claim 32 wherein said series comprises in sequence medium 1 and medium 2.

36. The process of claim 32 wherein said series comprises in sequence medium 1, medium 2 and medium 3.

37. The process of claim 32 wherein said series comprises in sequence medium 1, medium 2 and medium 4.

38. The process of claim 32 wherein said series comprises in sequence medium 1, medium 2, medium 4 and medium 3.

39. The process of claim 32 wherein said series comprises medium 3.

40. The process of claim 32 wherein said series comprises in sequence medium 3 and medium 4.

* * * * *